(12) United States Patent
Saisan et al.

(10) Patent No.: US 8,116,575 B1
(45) Date of Patent: Feb. 14, 2012

(54) SYSTEM FOR ANOMALY DETECTION USING SUB-SPACE ANALYSIS

(75) Inventors: Payam Saisan, San Diego, CA (US); Yuri Owechko, Newbury Park, CA (US); Swarup Medasani, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 963 days.

(21) Appl. No.: 12/072,697

(22) Filed: Feb. 26, 2008

(51) Int. Cl.
  *G06K 9/62* (2006.01)
  *G06K 9/46* (2006.01)
  *G06T 11/20* (2006.01)
  *G01N 33/48* (2006.01)
  *A61B 5/00* (2006.01)

(52) U.S. Cl. ........ 382/225; 382/160; 382/201; 382/203; 345/441; 600/300; 702/19

(58) Field of Classification Search .................. 382/224, 382/160, 225, 203, 201; 345/441; 600/300; 702/19
See application file for complete search history.

(56) References Cited

U.S. PATENT DOCUMENTS

| | | | |
|---|---|---|---|
| 7,761,240 B2 * | 7/2010 | Saidi et al. ...................... 702/19 |
| 2004/0147830 A1 | 7/2004 | Parker et al. | |
| 2005/0031183 A1 | 2/2005 | Wrigglesworth et al. | |
| 2005/0163278 A1 | 7/2005 | Metz et al. | |
| 2006/0104494 A1 * | 5/2006 | Collins et al. ................ 382/128 |

OTHER PUBLICATIONS

M. Turk and A. Pentland, "Face recognition using eigenfaces," Proc. IEEE Conference on Computer Vision and Pattern Recognition, 586-591, 1991.

C.M. Bishop, "Neural networks for pattern recognition," Oxford University Press, Oxford, 1995.

* cited by examiner

*Primary Examiner* — Kathleen Y Dulaney
(74) *Attorney, Agent, or Firm* — Tope-McKay & Assoc.

(57) ABSTRACT

Described is a system for anomaly detection to detect an anomalous object in an image, such as a concealed object beneath a person's clothing. The system is configured to generate a subspace model for a normal class using training images. The normal class represents normal objects in a common class. The system receives a novel image having an object in the common class. A set of geometric landmarks are identified in the object in the novel image for use in registering the image. The novel image is registered by warping the image so that the geometric landmarks coincide in the novel image and the training images, resulting in a warped novel image having an object. Thereafter, the system determines if the object in the warped novel image is anomalous by measuring the distance of the warped novel image from the subspace model. Finally, if anomalous, an operator is notified accordingly.

15 Claims, 8 Drawing Sheets

SYSTEM FOR ANOMALY DETECTION USING SUB-SPACE ANALYSIS

FIELD OF INVENTION

The present invention relates to an anomaly detection system and, more particularly, to a scanning system for detecting concealed objects using sub-space analysis.

BACKGROUND OF INVENTION

Figure 1:
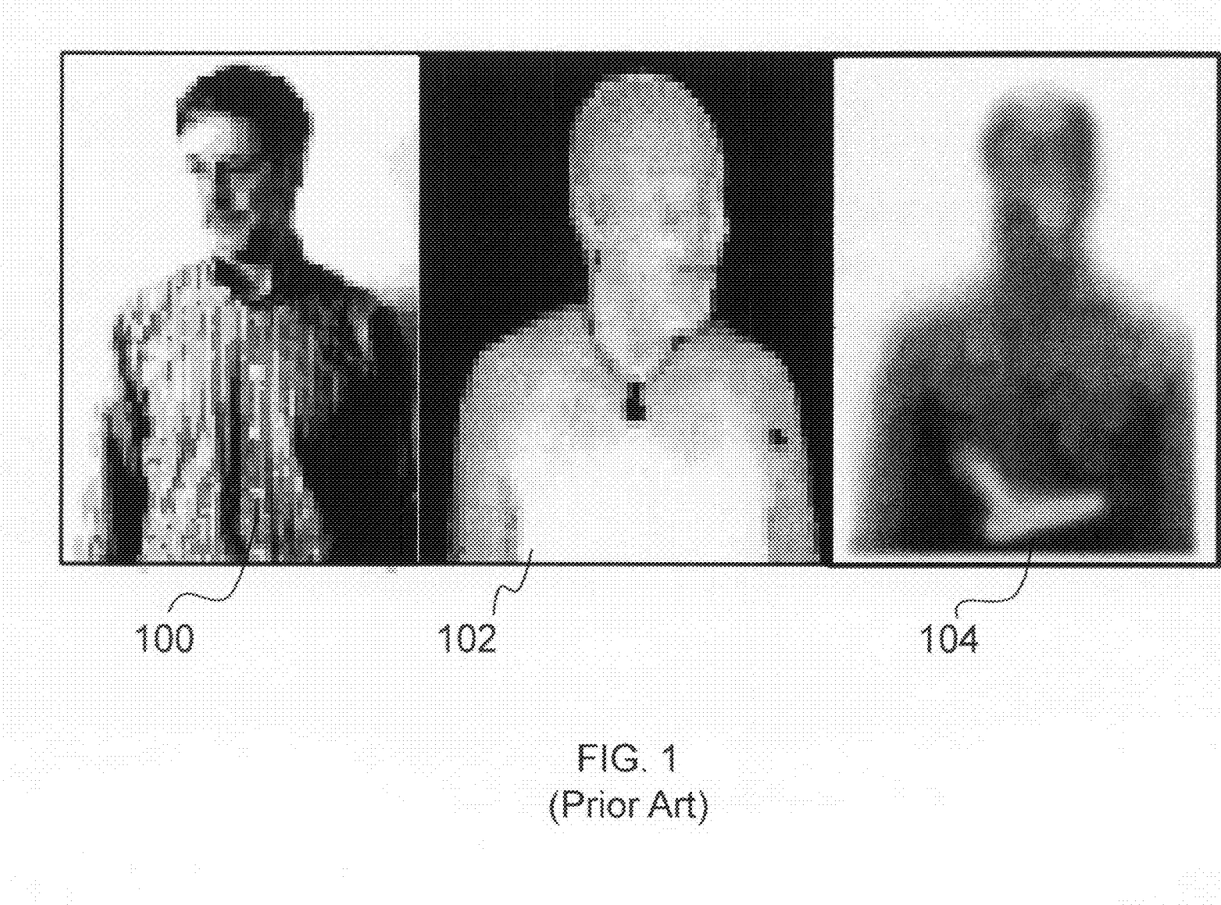
FIG. 1 is an illustration depicting different imaging modalities, including a visible image, millimeter wave, and backscatter X-ray.
Figure 2:
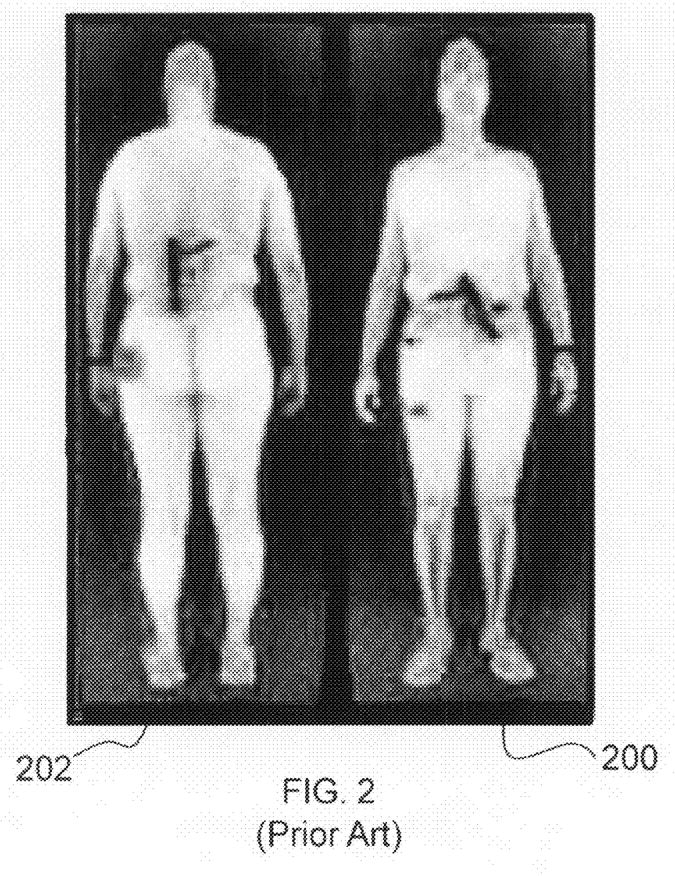
FIG. 2 is an illustration of a typical backscatter X-ray scan image.

The security industry is in need of technological innovation for producing automated image analysis systems for detecting concealed objects underneath a person's clothing. As shown in FIG. 1, existing imaging modalities include a visible image 100, a millimeter wave image (mmW) 102, and backscatter X-ray image 104. The objective in such a system is to automate the process so that a human operator is not required to look at raw data. However, as shown, a visible image 100 does not identify concealed objects. Alternatively, raw scans (such as the mmW 102 and backscatter X-ray 104 images) reveal what is underneath the clothing, which is the naked appearance of subjects. In the current state of technology, human operators have to directly inspect the scans displaying human subjects essentially in a naked form. Thus, such systems cannot be made operational in public for privacy reasons. Another example of such a raw scan is depicted in FIG. 2, which illustrates a frontal image 200 and a rear image 202 of a subject.

In almost all the existing mmW and backscatter X-ray scanning systems, the task of image inspection and analysis of the image content for the presence of concealed objects (e.g., weapons) is carried out manually by human operators. Although some attempts are being made at automating the process by device manufacturers such as Rapiscan Systems Inc. and Trex Enterprises Corporation, no fully automated system currently exists that can scan and reliably analyze two-dimensional (2D) image content for the presence of concealed objects. Rapiscan Systems Inc. is located at 2805 Columbia Street Torrance, Calif. 90503. Trex Enterprises Corporation is located at 10455 Pacific Center Court, San Diego, Calif. 92121.

Additionally, several recent patent applications have been filed that reveal a number of anomaly detection related systems devised within the context of medical imaging. The focus of related prior art on anomaly detection in the context of medical imaging is often on feature based anomalous/cancerous cell detection. For example, U.S. patent application Ser. No. 10/633,815, by Wrigglesworth et al., describes a system for detecting anomalous targets, namely cancerous cells. In this particular paradigm, a predefined number of features are extracted from a particular set of cell imagery. The features are then used to generate a probabilistic belief function to determine a probability that at least some of the cells in an image set are anomalous.

As another example, U.S. Pat. No. 7,072,435, issued to Metz et al., describes a system that processes computer tomography scans for detecting anomalous cancerous cells associated with lung cancer. The novelty in this particular patent is the use of CT imaging modality, while the algorithms for determining anomalies are somewhat standard computer aided detection (classification) methods.

As yet another example, U.S. patent application Ser. No. 10/352,867, by Parker et al., describes a system in which segmentation and localization of biomarkers, such as liver metastases and brain lesions, are cast as an anomaly detection problem. Statistical segmentation methods are used to identify biomarkers in the first image and the process is carried over to several subsequent images that are time evolutions of the biological construct (liver or brain tissue) that is under observation. The method relies on processing temporal sequences of three-dimensional medical imagery (instead of two-dimensional views).

The prior art is limited for these particular types of imagery. The limitation is primarily due to availability and the need for use of such scanning modalities for security purposes in the public domain. Prior art largely remains in the medical imaging domain where the task of anomaly detection is posed as identification of cancerous lesions. In the mmW and backscatter X-ray image analysis domain, device manufacturers have made attempts at bringing together a combination of off-the-shelf algorithms to analyze images for weapon detection, yet a reliable system does not currently exist that is able to detect weapons in such scans. The existing methods are often not tailored to the specific nature of the data. Thus, a continuing need exists for a system that uses a new analysis and detection theory to automatically identify concealed objects without violating a person's privacy expectations.

SUMMARY OF THE INVENTION

As mentioned above, the security industry is in need of an automated image analysis system for detecting concealed objects underneath a person's clothing. The present invention solves this need by providing a method, system, and computer program product for detecting an anomaly, such as a concealed object. In other words, the present invention identifies concealed objects by determining if an object in an image is anomalous and distinct from a normal object as provided in a training image.

The method comprises multiple acts, such as generating a model for a normal class using a training image, where the normal class represents normal objects in a common class. A novel image is received having an object in the common class. A set of geometric landmarks are identified in the object in the novel image for use in registering the image. The novel image is registered by warping the image so that the geometric landmarks coincide in the novel image and the training image, resulting in a warped novel image having an object. Thereafter, it is determined if the object in the warped novel image is anomalous. If anomalous, then an operator is notified that the object does not comply with a normal object and could possibly include a concealed item (such as a weapon), prompting the operator to further search the object or subject. As another example, an output can be an update to a database that the novel image deviates from the common class to such an extent that a weapon or contraband may be shown in the novel image.

In another aspect, the act of generating a model for the normal class further comprises several additional acts. For example, a plurality of images representing a normal class is received, where each image has an object in a common class. Additionally, a set of geometric landmarks are identified in the object for use in registering the images. Further, the images are registered by warping the images so that the geometric landmarks coincide in each of the images in a warped configuration (the images now being a set of training images). An Eigenspace analysis is performed on the training images to construct a low-dimensional image subspace model of the normal class. A distance is computed between each of the training images to the low-dimensional image subspace model to generate a probability distribution of distances from the normal class to the subspace model. Finally, a probability distribution is generated of distances from the normal class to the subspace model.

In yet another aspect, the act of determining if the object in the warped novel image is anomalous comprises several additional acts. For example, a distance is computed between the warped novel image and a subspace model. The distance is input into a probability distribution function to generate a probability of being anomalous. Finally, the object is classified as anomalous if the probability satisfies a predetermined threshold.

In another aspect, the present invention further comprises an act of generating a probability distribution of distances from an anomalous class to the subspace model.

The act of generating a probability distribution of distances from an anomalous class to the subspace model further includes several additional acts. For example, a plurality of training images is received of the anomalous class. Additionally, a distance is computed of each of the training images to the low-dimensional image subspace model to generate the probability distribution of distances from an anomalous class to the subspace model.

In yet another aspect, the act of determining if the object in the warped novel image is anomalous further comprises several additional acts. For example, a distance is computed between the warped novel image and a subspace model. A point of intersection is identified between each of the probability distributions, where the point of intersection defines a threshold to be used in determining a likelihood of being anomalous. It is then determined if the distance satisfies the threshold to classify the object as anomalous or normal.

Finally, as can be appreciated by one skilled in the art, the present invention also includes a computer program product and a system for detecting an anomaly. The computer program product comprises computer-readable instruction means stored on a computer-readable medium that are executable by a computer for causing the computer to perform the operations and acts described herein. Further, the system comprises one or more processors that are configured to perform the described operations and acts.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to an anomaly detection system and, more particularly, to a scanning system for detecting concealed objects using sub-space analysis. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a description of various principal aspects of the present invention is provided. Subsequently, an introduction provides the reader with a general understanding of the present invention. Finally, details of specific aspects of the present invention are provided to give the reader or more detailed understanding.

(1) Principal Aspects

The present invention has three "principal" aspects. The first is an anomaly detection system. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions means stored on a computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 3:
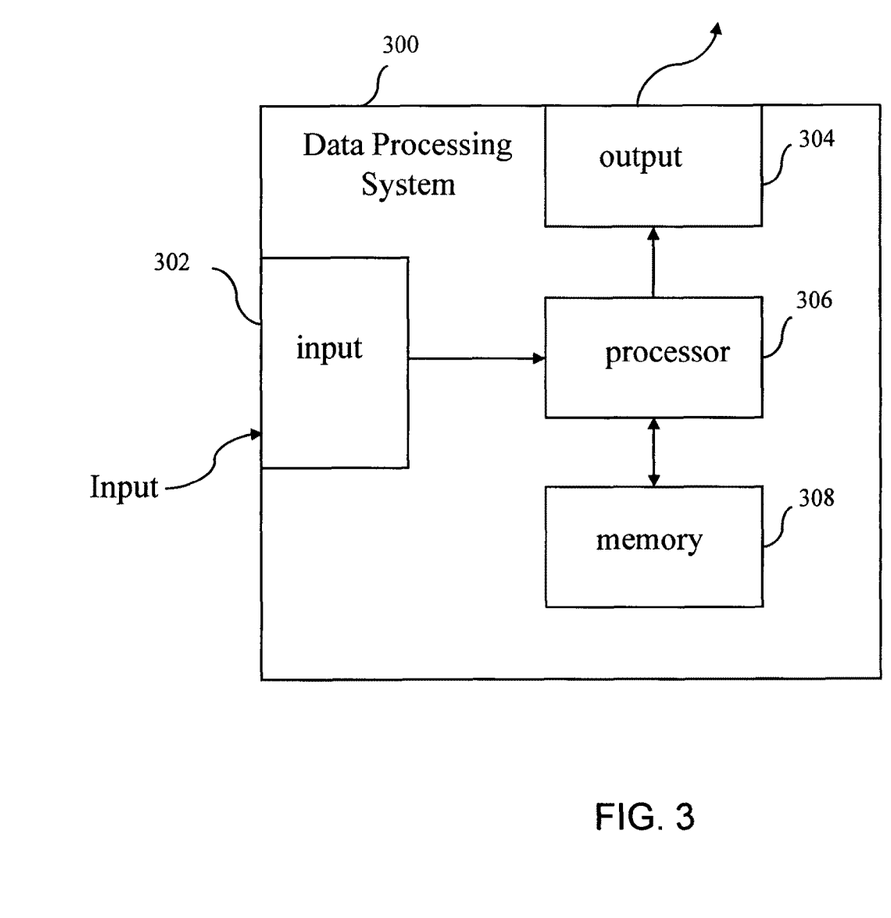
FIG. 3 is a block diagram depicting the components of an image processing system of the present invention.

A block diagram depicting the components of an anomaly detection system of the present invention is provided in FIG. 3. The anomaly detection system 300 comprises an input 302 for receiving information from at least one sensor for use in detecting an anomaly in an image. Note that the input 302 may include multiple "ports." Typically, input is received from at least one sensor, non-limiting examples of which include video image sensors. An output 304 is connected with the processor for providing information regarding image (or an anomaly in the image) to other systems in order that a network of computer systems may serve as an anomaly detection system. Output may also be provided to other devices or other programs; e.g., to other software modules, for use therein. The input 302 and the output 304 are both coupled with a processor 306, which may be a general-purpose computer processor or a specialized processor designed specifically for use with the present invention. The processor 306 is coupled with a memory 308 to permit storage of data and software that are to be manipulated by commands to the processor 306.

Figure 4:
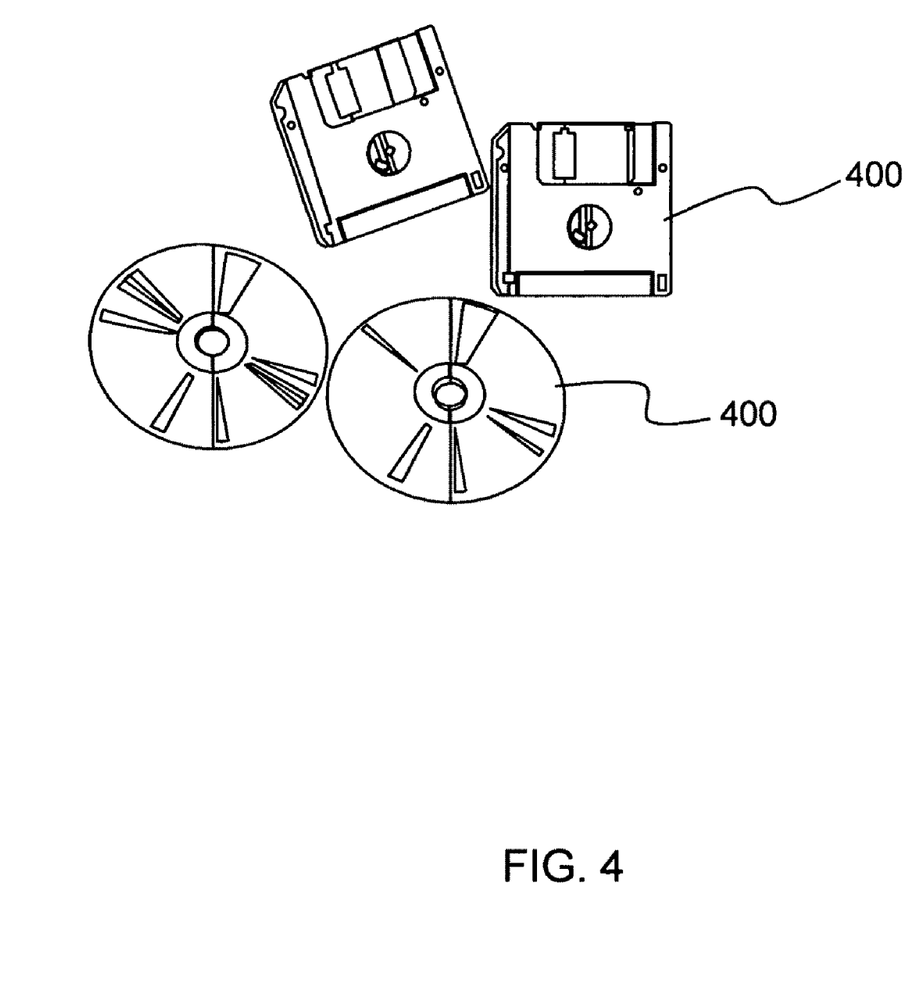
FIG. 4 is a computer program product embodying the present invention.

An illustrative diagram of a computer program product embodying the present invention is depicted in FIG. 4. The computer program product 400 is depicted as an optical disk such as a CD or DVD. However, as mentioned previously, the computer program product generally represents computer-readable instruction means stored on any compatible computer-readable medium. The term "instruction means" as used with respect to this invention generally indicates a set of operations to be performed on a computer, and may represent pieces of a whole program or individual, separable, software modules. Non-limiting examples of "instruction means" include computer program code (source or object code) and "hard-coded" electronics (i.e., computer operations coded into a computer chip). The "instruction means" may be stored in the memory of a computer or on a computer-readable medium such as a floppy disk, a CD-ROM, and a flash drive.

(2) Introduction

Imaging technology to detect objects hidden underneath layers of clothing is a recent and rapidly developing field. Backscatter X-ray scanning devices have been in use for some time in prisons for scanning inmates for the presence of concealed weapons. More recently, millimeter wave (mmW)-based imaging devices are being developed with the same intent by a number of companies. However, such devices are unmarketable for use in the public domain due to privacy issues involved in the nature of scans (scans reveal humans in naked form).

Addressing the need for privacy, the present invention can be used to analyze such scans automatically for the presence of anomalous objects (such as weapons), eliminating the need for inspection of scans by a human operator. Such systems can be deployed in airports and elsewhere where there is a need for inspection of subjects for the presence of concealed objects.

Thus, the present invention is a system and method for anomaly detection through the automatic analysis of mmW and backscatter X-ray type scans of human subjects. The present invention detects anomalous objects inconsistent with the normal anatomical appearance of the human body and therefore can be used for detection of objects concealed underneath layers of clothing. The present invention has been developed using an analog problem where an attempt is made to detect people wearing glasses and discriminate them from those without glasses. While the method is tested for detecting anomalies on faces, the idea is to be extended and applied directly to full body scans resulting from mmW and backscatter X-ray scanning devices.

A novel aspect of the present invention is the use of shape registration in conjunction with low-dimensional image subspace analysis for formulating a single class anomaly detection paradigm. The paradigm is used to analyze deviations of human body parts from their normal form as depicted in the specific imaging modalities of mmW and backscatter X-ray imagery. The method can learn the general appearance of the human body part without conspicuous objects attached to it, and then attempt to single out anomalous human scan images, namely those inconsistent with the normal anatomical appearance of the body. The idea is to use anomaly detection to single out what an un-armed human scan looks like and then attempt to detect any deviations from that model and alert device operators of the possible presence of concealed and potentially dangerous objects. A more detailed description of the present invention is provided below.

(3) Details of Specific Aspects

Anomaly detection according to the present invention relies on learning principal characteristics of a normal class. It is a one-class comparison, in that there is training information available only on the "normal" class. Everything outside of the normal class will be considered anomalous.

Figure 5:
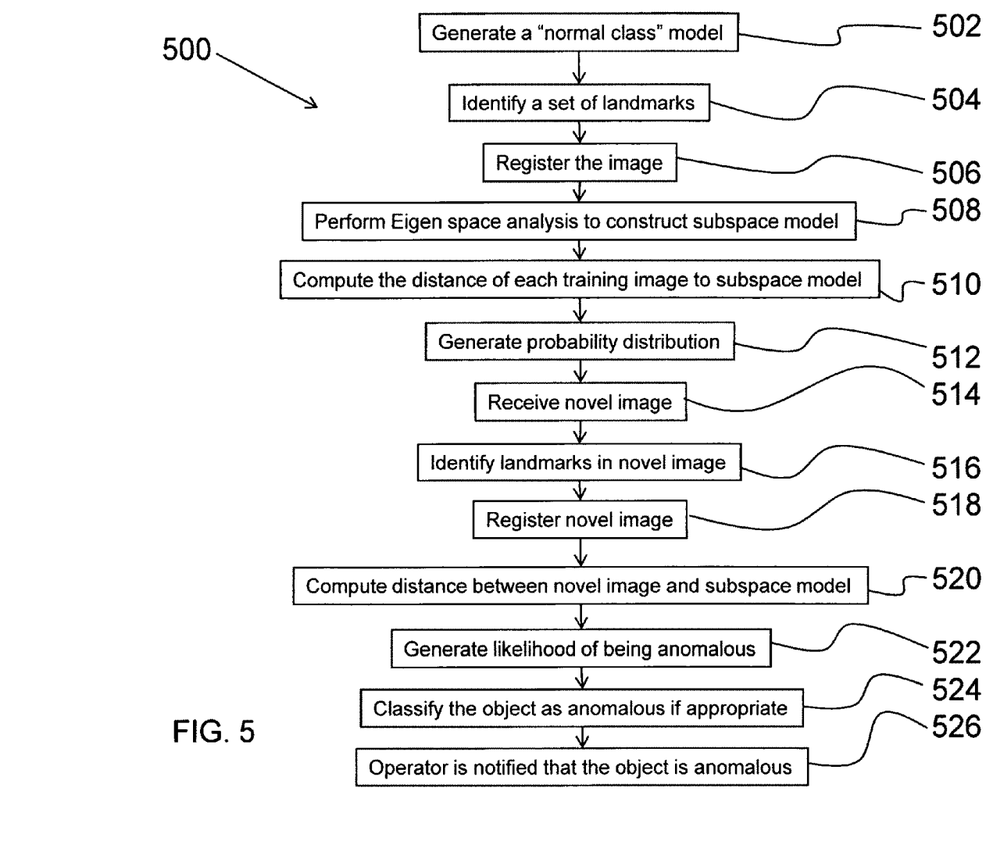
FIG. 5 is a flow chart illustrating a process of anomaly detection according to the present invention.

FIG. 5 is a flowchart 500 illustrating the basic steps for anomaly detection according to the present invention. As shown in FIG. 5, the system is configured to generate a model 502 for the normal class. In doing so, the system receives a plurality of images representing the normal class, with each image having an object in a common class (e.g., such as eyes). Next, the system identifies a set of geometric landmarks 504 in the object for use in registering the image. The image is registered 506 by warping the images so that the geometric landmarks coincide in each of the images in a warped configuration. Thus, once registered, the images are operable as a set of training images. An Eigenspace analysis is then performed 508 on the training images to construct a low-dimensional image subspace model of the normal class. The distance is then computed 510 between each of the training images to the low-dimensional image subspace model. The distances are computed to generate a probability distribution of distances from the normal class to the subspace model.

The distance is defined as the Euclidean distance between vectorized images. Any image can be represented as a point or vector in a high-dimensional space where each pixel is a dimension. The distance between a training image and the subspace model is described as the Euclidean distance between the input image and the projection of the training image onto the subspace, which is also an image. The projection is formed by adding a weighted sum of the first N eigenvectors of the training set, calculated using standard principal component analysis (PCA) analysis. PCA is a well known procedure to one skilled in the art and can be found in the literature, such as in "Pattern Classification," by Duda, Hart, and Stork, John Wiley, 2001. The weights are given by the inner product of the input image with the corresponding eigenvector. N is determined a priori as part of the modeling process. The distance is then calculated as the square root of the sum of the squares of the differences between corresponding pixel values in the two images.

A probability distribution is then generated 512 of the distances from the normal class to the subspace model. Once the probability distribution is generated 512, the system is operable for receiving a novel image 514 having an object in the common class. A set of geometric landmarks is then identified 516 in the object in the novel image for using in registering the image. The novel image is then registered 518 by warping the image so that the geometric landmarks coincide in the novel image and the training images. The distance between the warped novel image and the subspace model is thereafter computed 520. The distance is then input into the probability distribution function to generate likelihood of being anomalous 522. If the probability satisfies a predetermined threshold, then the object is considered anomalous 524. Finally, if the object is considered anomalous, then an operator is notified that the object is anomalous 526. For example, the system could provide a signal to an operator or an update to a database that the novel image deviates from the common class to such an extent that a weapon or contraband may be shown in the novel image. If the present invention is part of a security system, then the output could be a determination that the novel image shows contraband and further investigation by a human operator is required As can be appreciated by one skilled in the art, the present invention can be applied to a wide variety of objects. For example, since a hidden weapon image dataset was lacking, the present invention was demonstrated using an analogous problem of detecting faces with glasses by training only on faces without glasses. Here, the normal class subspace is represented by a reduced set of basis vectors in the space of face images. The method draws on a well-known concept of eigenfaces, as described by M. Turk and A. Pentland, in "Face recognition using eigenfaces," *Proc. of the Institute of Electrical and Electronics Engineers (IEEE) Conference on Computer Vision and Pattern Recognition,* 586-591 (1991). The basic vectors or eigenfaces are generated using principal component analysis.

The present invention was demonstrated using a PCA-induced eight-dimensional sub-space to represent the space of "face without glasses." With the subspace at hand, for a given novel image, its distance can be computed between each novel image to the "face without glasses" subspace. The idea here is that "faces with glasses" should have a generally larger distance to the "face without glasses" subspace.

Figure 6:
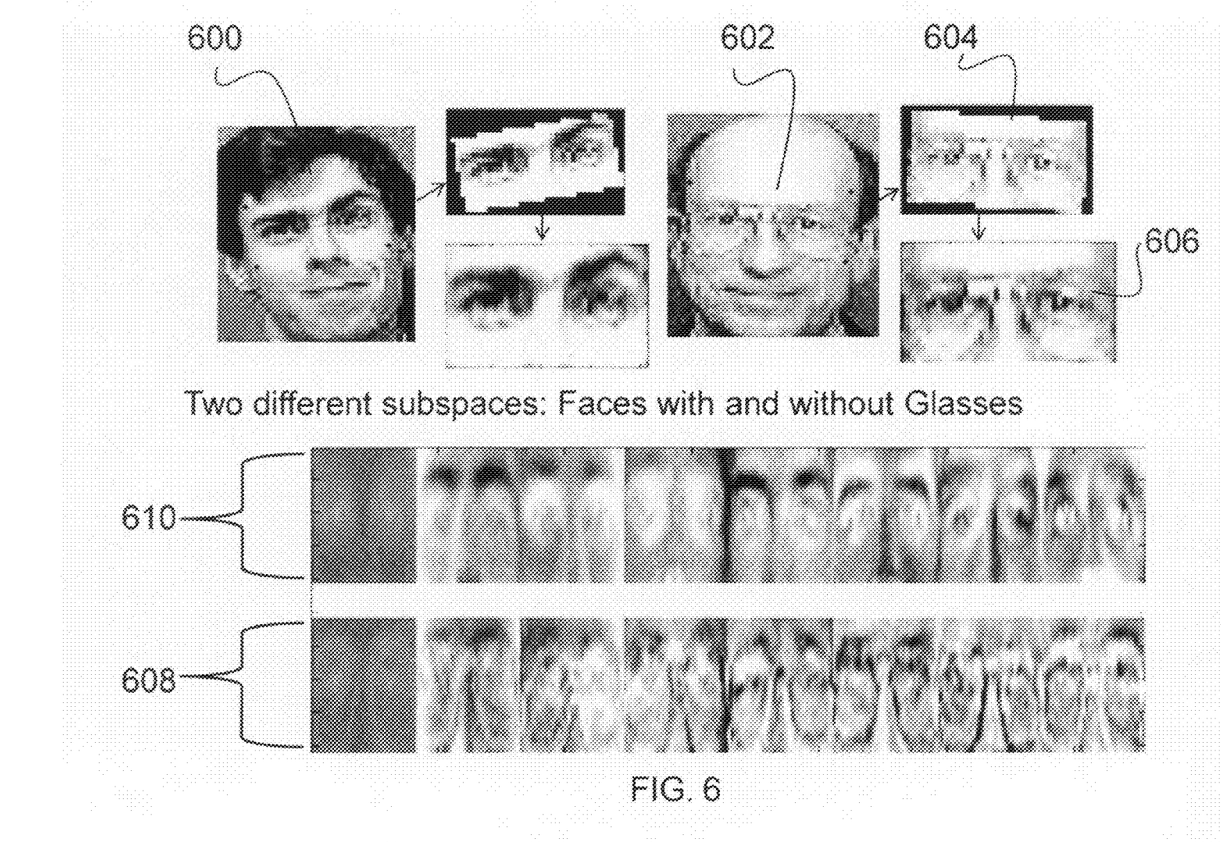
FIG. 6 is an illustration of face alignment/registration and warping based on anatomical landmarks, such as the location of a person's eyes.

As shown in FIG. 6, a key component to the present invention is face alignment/registration and warping. The alignment/registration and warping is based on anatomical landmarks, such as the location of the eyes. As can be appreciated by one skilled in the art, the present invention is not limited thereto as it can be applied to other landmarks, such as shoulders, ears, chest and back, etc.

Illustrated in FIG. 6 are the original images of the "face without glasses" 600 and the "face with glasses" 602. The original images are then cropped to reflect the selected landmarks, thereby generating piecewise images 604. Thereafter, the images are warped to generate the registered face images 606 that include the landmarks. In other words, piecewise affine warping was used to generate registered face images. The lower image depicts the eight-dimensional subspaces for both the face with glasses 608 and face without glasses 610. The normal class of face subspace (i.e., face without glasses 610) exhibits a structure that is clearly distinct from the anomalous class (i.e., face with glasses 608).

Shape registration across the image ensemble is a key step in capturing the essential appearance characteristics of the normal class. In other words, by removing geometric variations, the appearance characteristics of the normal class can be obtained. Shape registration is based on anatomical landmarks. For example and as illustrated in FIG. 6, the landmarks can be the location of the eyes. In a more general context, any appearance-based feature and landmark-based registration that can remove/reduce geometric variations within the normal class training ensemble can be used. These methods can be extended to full body shape registration in a similar way. The area of geometric shape registration is a large area of study within the medical imaging community. Thus, powerful computational tools (image-based registration) are available for this aspect of the present invention; a non-limiting example of such a tool includes VisiQuest by AccuSoft Corporation. AccuSoft Corporation is located at 71 Lyman Street, Northborough, Mass., 01532.

Figure 7A:
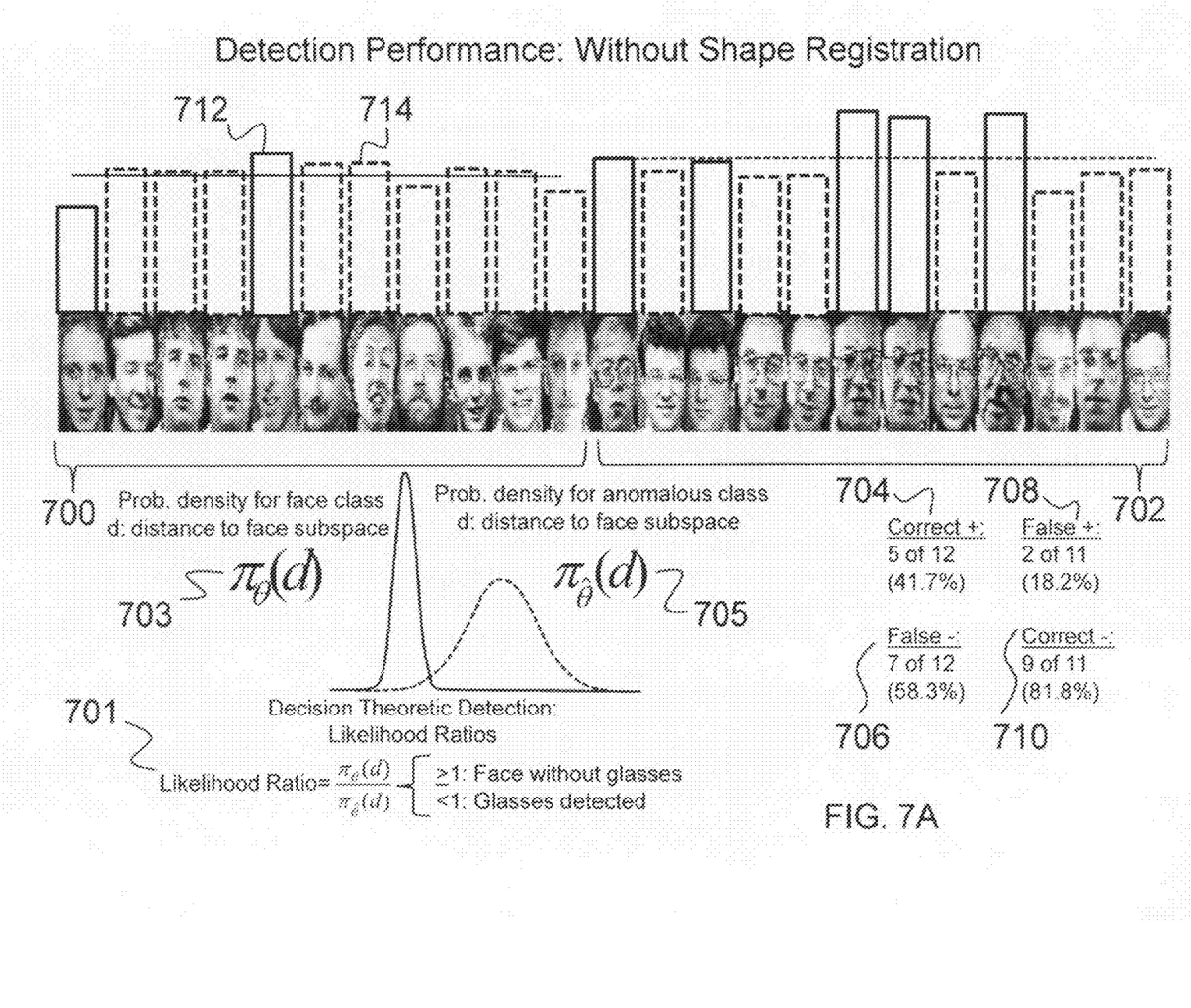
FIG. 7A is an illustration of anomaly detection without a shape registration step.

FIG. 7A illustrates the results of an anomaly detection experiment (detection of faces with glasses) carried out on a novel data set, without shape registration. The experiments were carried out using The Database of Faces, by AT&T Laboratories Cambridge, located at the William Gates Building, 15 JJ Thomson Avenue, Cambridge, CB3 0FD, United Kingdom. The experiment included eleven raw images of faces without glasses 700 and twelve raw images of faces with glasses 702.

The experimental results for the raw images of faces 700 and 702 clearly indicate that a simple direct PCA subspace analysis on the images does not lead to good results. For example, the analysis correctly identified (i.e., correct positive 704) the faces with glasses 41.7 percent of the time, while making a false identification (i.e., false negative 706) 58.3 percent of the time. Alternatively, the analysis incorrectly identified the faces without glasses as having glasses (i.e., false positive 708) 18.2 percent of the time, while correctly identifying the faces without glasses as not having glasses (i.e., correct negative 710) 81.8 percent of the time. The images that were identified as having glasses are illustrated with a bar graph having a solid line 712 while the images that were identified as not having glasses are illustrated with a bar graph having a dashed line 714. The relative heights of each bar in the bar graph is indicative of the Euclidean distance between the novel image and the eight-dimensional face subspace.

The eight-dimensions for a novel instance of a data point (an image) are obtained by taking the inner product of the image with the eight most significant eigenvectors provided by the PCA operation previously, namely the subspace vectors. The inner product between two vectors is a well known mathematical operation.

Thus, the detection decision was based on the Euclidean distance between the novel image and the eight-dimensional face sub-space. The final binary classification between the two categories was done using a decision theoretic method of likelihood ratios 701 that relies on the statistics (i.e., probability density) of the distance for non-glasses 700 and glasses 702 categories. The probability density includes the probability density for the non-glasses 700 class (i.e., face class probability density 703) and the probability density for the glasses 702 class (i.e., anomalous class probability density 705), which are derived from the distance (d) to their respective face subspaces.

Probability density is assumed to be a continuous function. An approximation of a continuous probability density can be an array of numbers. The distance computed earlier is used as the input to a probability density function to yield the corresponding probability at that distance. The ratio of corresponding probabilities for the normal and anomalous class's probability density function is the likelihood ratio. The probability density function is assumed to be Gaussian. The statistics analyzed are the mean and the variance.

The process for binary detection decision using likelihood ratios is as follows. Given the subspace distance to the normal class, the statistics of a novel training set of images can be analyzed. Given data on both normal and anomalous classes, the conditional probability distributions can be estimated corresponding to subspace distances for these classes. The method of likelihood ratios allows for the final binary decision on whether a novel image is more likely to contain a hidden object or not based on the ratio of the likelihoods. If it is assumed that both the anomalous and normal objects are equally likely, then it can be easily shown that the ratio of conditional densities or likelihood ratios is the optimal way to minimize risk and misclassification error.

The anomaly detection is very sensitive to statistics of the normal class. The raw face data in the database are not fully shape-registered. Thus, there is tremendous variability in appearance due to the rigid motion of the faces and the inter-personal shape differences among different faces. In order to reduce the variability in the face subspace, the present invention includes a shape-based alignment and registration of the faces in the training set. Shape registration, in this example, is based on location and orientation of anatomical landmarks, namely the eyes (as illustrated in FIG. 6).

Figure 7B:
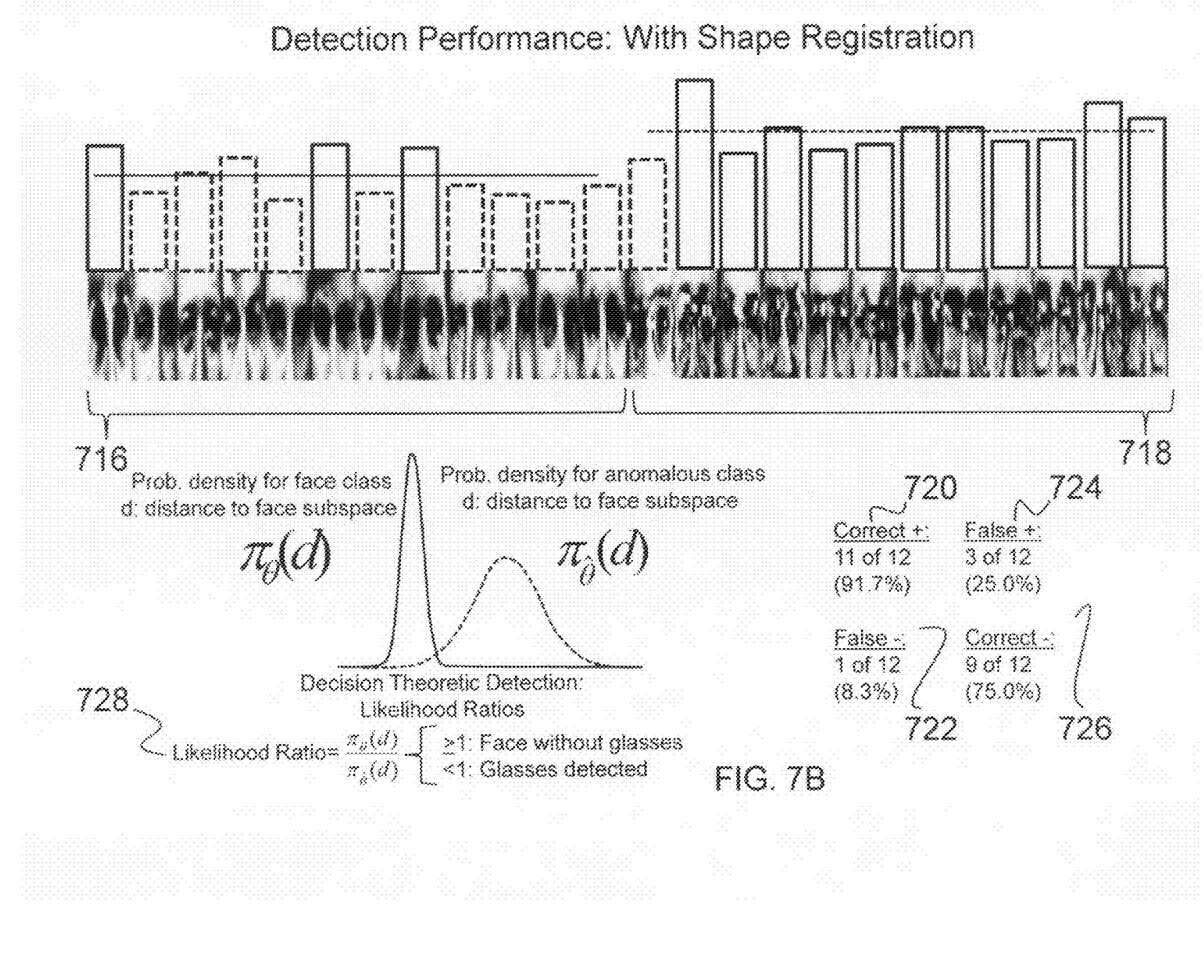
FIG. 7B is an illustration of anomaly detection with a shape registration step.

As shown in FIG. 7B, the anomaly detection experiments were repeated with shape-registered face data. The experiment included twelve shape-registered images without glasses 716 and with glasses 718. FIG. 7B illustrates the results of the experiment, which indicate that the system was able to detect glasses with a relatively high success rate. For example, the analysis correctly identified (i.e., correct positive 720) the faces with glasses 91.7 percent of the time, while making a false identification (i.e., false negative 722) 8.3 percent of the time. Alternatively, the analysis incorrectly identified the faces without glasses as having glasses (i.e., false positive 724) 25.0 percent of the time, while correctly identifying the faces without glasses as not having glasses (i.e., correct negative 726) 75.0 percent of the time.

As was the case above, the detection decision was based on the Euclidean distance between the novel image and the eight-dimensional face sub-space. The final binary classification between the two categories was done using a decision theoretic method of likelihood ratios 728 that relies on the statistics of the distance for non-glasses 716 and glasses 718 categories.

It should be noted that although this embodiment of the invention refers to an entire image being used for the subspace analysis, the method can be extended to work with parts of an image. In a more general scenario, the registered subspace analysis mentioned above can be completed for each part of the image separately. Although this introduces some additional complexity, it has the advantage of picking anomalous objects of varying sizes. In addition, it allows for an increased accuracy by placing a priori models on regions of the image that are more likely to contain anomalous or hidden objects.

What is claimed is:

1. A computer implemented method for detecting an anomaly, comprising an act of causing a processor to perform operations of:
   generating a model for a normal class using a training image, the normal class representing normal objects in a common class, wherein the operation of generating a model for the normal class further comprises operations of:
      receiving a plurality of images representing the normal class, each image having an object in a common class;
      identifying a set of geometric landmarks in the object for use in registering the images;
      registering the images by warping the images so that the geometric landmarks coincide in each of the images in a warped configuration, the images now being a set of training images;
      performing an Eigenspace analysis on the training images to construct a low-dimensional image subspace model of the normal class;
      computing a distance between each of the training images and the low-dimensional image subspace model; and
      generating a probability distribution of distances from the normal class to the subspace model;
   receiving a novel image having an object in the common class;
   identifying a set of geometric landmarks in the object in the novel image for use in registering the image;
   registering the novel image by warping the image so that the geometric landmarks coincide in the novel image and the training image, resulting in a warped novel image having an object;
   generating a probability distribution of distances from an anomalous class to the subspace model;
   determining if the object in the warped novel image is anomalous by further performing operations of:
      computing a distance between the warped novel image and a subspace model;
      identifying a point of intersection between the probability distribution of the normal class and the probability distribution of the anomalous class, the point of intersection defining a threshold to be used in determining a likelihood of being anomalous; and
      determining if the distance satisfies the threshold to classify the object as anomalous or normal; and
   notifying an operator if the object in the warped novel image is determined to be anomalous.

2. A computer implemented method as set forth in claim 1, wherein the operation of determining if the object in the warped novel image is anomalous further comprises operations of:
   computing a distance between the warped novel image and the subspace model;
   inputting the distance into a probability distribution function to generate a probability of being anomalous; and
   classifying the object as anomalous if the probability satisfies a predetermined threshold.

3. A computer implemented method as set forth in claim 1, where the operation of generating a probability distribution of distances from an anomalous class to the subspace model further comprises operations of:
   receiving a plurality of training images of the anomalous class; and
   computing a distance of each of the training images to the low-dimensional image subspace model to generate the probability distribution of distances from an anomalous class to the subspace model.

4. A computer implemented method as set forth in claim 1, wherein the operation of determining if the object in the warped novel image is anomalous further comprises operations of:
   computing a distance between the warped novel image and a subspace model;
   inputting the distance into a probability distribution function to generate a probability of being anomalous; and
   classifying the object as anomalous if the probability satisfies a predetermined threshold.

5. A computer implemented method as set forth in claim 1, further comprising an operation of generating a probability distribution of distances from an anomalous class to a subspace model.

6. A computer program product for detecting an anomaly, the computer program product comprising computer-readable instruction means stored on a non-transitory computer-readable medium that are executable by a computer having a processor for causing the processor to perform operations of:
   generating a model for a normal class using a training image, the normal class representing normal objects in a common class, wherein the operation of generating a model for the normal class further comprises operations of:

receiving a plurality of images representing the normal class, each image having an object in a common class;

identifying a set of geometric landmarks in the object for use in registering the images;

registering the images by warping the images so that the geometric landmarks coincide in each of the images in a warped configuration, the images now being a set of training images;

performing an Eigenspace analysis on the training images to construct a low-dimensional image subspace model of the normal class;

computing a distance between each of the training images and the low-dimensional image subspace model; and generating a probability distribution of distances from the normal class to the subspace model;

receiving a novel image having an object in the common class;

identifying a set of geometric landmarks in the object in the novel image for use in registering the image;

registering the novel image by warping the image so that the geometric landmarks coincide in the novel image and the training image, resulting in a warped novel image having an object;

generating a probability distribution of distances from an anomalous class to the subspace model;

determining if the object in the warped novel image is anomalous by further performing operations of:

computing a distance between the warped novel image and a subspace model;

identifying a point of intersection between the probability distribution of the normal class and the probability distribution of the anomalous class, the point of intersection defining a threshold to be used in determining a likelihood of being anomalous; and determining if the distance satisfies the threshold to classify the object as anomalous or normal; and notifying an operator if the object in the warped novel image is determined to be anomalous.

7. A computer program product as set forth in claim 6, further comprising instruction means are executable by a computer having a processor for causing the processor to perform operations of:

computing a distance between the warped novel image and the subspace model;

inputting the distance into a probability distribution function to generate a probability of being anomalous; and classifying the object as anomalous if the probability satisfies a predetermined threshold.

8. A computer program product as set forth in claim 6, further comprising instruction means that are executable by a computer having a processor for causing the processor to perform operations of:

receiving a plurality of training images of the anomalous class; and computing a distance of each of the training images to the low-dimensional image subspace model to generate the probability distribution of distances from an anomalous class to the subspace model.

9. A computer program product as set forth in claim 6, further comprising instruction means that are executable by a computer having a processor for causing the processor to perform operations of:

computing a distance between the warped novel image and a subspace model;

inputting the distance into a probability distribution function to generate a probability of being anomalous; and classifying the object as anomalous if the probability satisfies a predetermined threshold.

10. A computer program product as set forth in claim 6, further comprising instruction means that are executable by a computer having a processor for causing the processor to perform an operation of generating a probability distribution of distances from an anomalous class to a subspace model.

11. A system for detecting an anomaly, the system comprising one or more processors configured to perform operations of:

generating a model for a normal class using a training image, the normal class representing normal objects in a common class, wherein the operation of generating a model for the normal class further comprises operations of:

receiving a plurality of images representing the normal class, each image having an object in a common class;

identifying a set of geometric landmarks in the object for use in registering the images;

registering the images by warping the images so that the geometric landmarks coincide in each of the images in a warped configuration, the images now being a set of training images;

performing an Eigenspace analysis on the training images to construct a low-dimensional image subspace model of the normal class;

computing a distance between each of the training images and the low-dimensional image subspace model; and generating a probability distribution of distances from the normal class to the subspace model;

receiving a novel image having an object in the common class;

identifying a set of geometric landmarks in the object in the novel image for use in registering the image;

registering the novel image by warping the image so that the geometric landmarks coincide in the novel image and the training image, resulting in a warped novel image having an object;

generating a probability distribution of distances from an anomalous class to the subspace model;

determining if the object in the warped novel image is anomalous by further performing operations of:

computing a distance between the warped novel image and a subspace model;

identifying a point of intersection between the probability distribution of the normal class and the probability distribution of the anomalous class, the point of intersection defining a threshold to be used in determining a likelihood of being anomalous; and determining if the distance satisfies the threshold to classify the object as anomalous or normal; and notifying an operator if the object in the warped novel image is determined to be anomalous.

12. A system as set forth in claim 11, wherein in determining if the object in the warped novel image is anomalous, the system is further configured to perform operations of:

computing a distance between the warped novel image and the subspace model;

inputting the distance into a probability distribution function to generate a probability of being anomalous; and classifying the object as anomalous if the probability satisfies a predetermined threshold.

13. A system as set forth in claim 11, where in generating a probability distribution of distances from an anomalous class to the subspace model, the system is further configured to perform operations of:

receiving a plurality of training images of the anomalous class; and computing a distance of each of the training images to the low-dimensional image subspace model to generate the probability distribution of distances from an anomalous class to the subspace model.

14. A system as set forth in claim 11, wherein in determining if the object in the warped novel image is anomalous, the system is further configured to perform operations of:

computing a distance between the warped novel image and a subspace model;

inputting the distance into a probability distribution function to generate a probability of being anomalous; and classifying the object as anomalous if the probability satisfies a predetermined threshold.

15. A system as set forth in claim 11, wherein the system is further configured to perform an operation of generating a probability distribution of distances from an anomalous class to a subspace model.

* * * * *